(12) United States Patent
Ochiai

(10) Patent No.: US 8,403,947 B2
(45) Date of Patent: Mar. 26, 2013

(54) METHOD OF SUTURING

(76) Inventor: Derek H. Ochiai, Great Falls, VA (US)

( * ) Notice: Subject to any disclaimer, the term of this patent is extended or adjusted under 35 U.S.C. 154(b) by 333 days.

(21) Appl. No.: 12/486,088

(22) Filed: Jun. 17, 2009

(65) Prior Publication Data

US 2009/0318958 A1      Dec. 24, 2009

Related U.S. Application Data

(60) Provisional application No. 61/073,116, filed on Jun. 17, 2008.

(51) Int. Cl.
*A61B 17/04* (2006.01)
(52) U.S. Cl. ..................... 606/144
(58) Field of Classification Search ............... 606/139, 606/144, 148, 222, 223, 224; 112/222–224; 128/898
See application file for complete search history.

(56) References Cited

U.S. PATENT DOCUMENTS

| | | | |
|---|---|---|---|
| 109,427 A | 11/1870 | Landfear | |
| 166,993 A | 8/1875 | Lascell | |
| 287,592 A * | 10/1883 | Thimonnier et al. | 112/199 |
| 523,554 A | 7/1894 | Stickney | |
| 703,941 A | 7/1902 | Merrick | |
| 1,060,107 A | 4/1913 | Martin | |
| 1,955,974 A * | 4/1934 | Poole | 112/53 |
| 3,408,751 A * | 11/1968 | Levy | 36/104 |
| 3,581,688 A | 6/1971 | Ketterer | |
| 3,754,693 A | 8/1973 | Herr | |
| 3,834,599 A | 9/1974 | Herr | |
| 4,068,605 A | 1/1978 | Matthews | |
| 4,527,564 A | 7/1985 | Eguchi et al. | |
| 4,644,953 A * | 2/1987 | Lahodny et al. | 606/174 |
| 5,437,680 A | 8/1995 | Yoon | |
| 5,474,565 A | 12/1995 | Trott | |
| 5,676,675 A | 10/1997 | Grice | |
| 5,934,212 A | 8/1999 | Gitlin et al. | |
| 6,679,889 B1 * | 1/2004 | West et al. | 606/88 |
| 6,746,456 B2 * | 6/2004 | Xiao | 606/144 |
| 6,896,686 B2 | 5/2005 | Weber | |
| 7,118,583 B2 | 10/2006 | O'Quinn et al. | |
| 2003/0045891 A1 * | 3/2003 | Yamamoto et al. | 606/144 |

OTHER PUBLICATIONS

STIC Search Results from Aug. 2012.*

* cited by examiner

*Primary Examiner* — Ryan Severson
*Assistant Examiner* — Rachel S Papeika
(74) *Attorney, Agent, or Firm* — Millen, White, Zelano, Branigan, P.C.

(57) ABSTRACT

The invention relates to a method of suturing. Briefly, a portion of a needle having a continuous suture thread running through the eye is advanced through a first location on a first side of a tissue. When the needle is withdrawn from said tissue a suture loop is retained on a second side of said tissue. This can be repeated to obtain as many suture loops as desired on additional locations of the tissue. When all the desired suture loops are formed the needle is advanced all the way through the tissue and a single strand of suture thread is passed through each suture loop on the second side of the said tissue. Thus, one continuous suture forms the suture loop(s) and engages the sutured loops. In a preferred embodiment the needle eye, through which the suture thread runs, is located in the tip portion of said needle. It is also preferred that the needle is curved. The tissue may be, for example, a tendon (e.g., patellar), a ligament, or a graft. In yet another embodiment the suturing method of the present invention involves passing a suture through a tendon to achieve maximum suture fixation strength, as well as a method of securing the tendon to bone that allows for accelerated tendon healing to bone. The invention also relates to a construct prepared by the suture methods of the present invention.

10 Claims, 5 Drawing Sheets

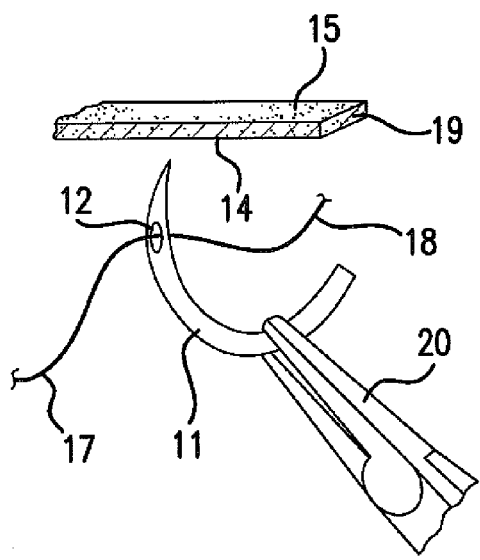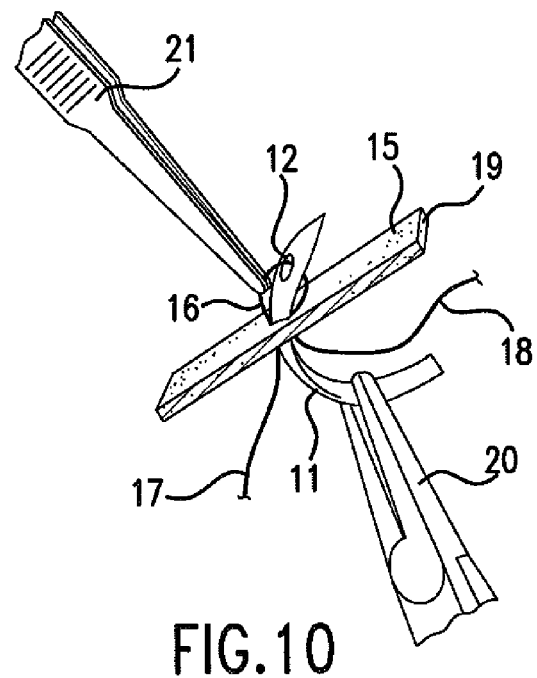
FIG.9　　　　　　FIG.10
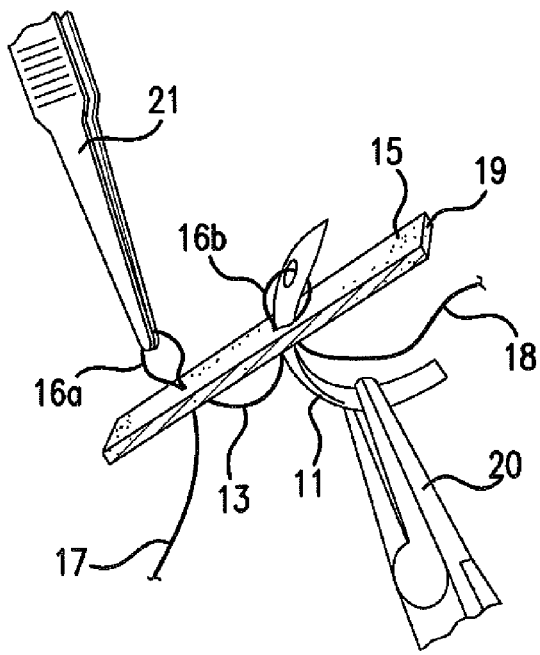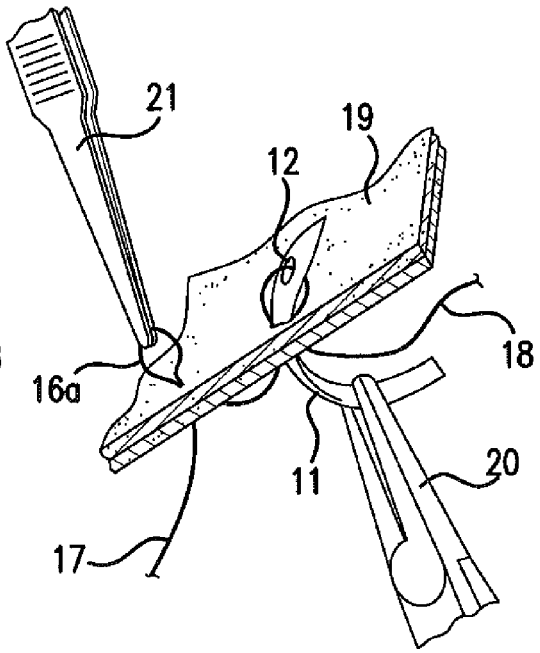
FIG.11　　　　　　FIG.12

METHOD OF SUTURING

This application claims the benefit of the filing date of U.S. Provisional Application Ser. No. 61/073,116 filed Jun. 17, 2008.

FIELD OF INVENTION

The present invention relates a method of suturing.

BACKGROUND OF THE INVENTION

Medical practitioners frequently use sutures to repair tissue and facilitate healing. Sutures can be used to close various openings (e.g., cuts, punctures, and incisions). They may also be used to anchor and tension grafts and ligaments. Because of their importance and frequent use, several types of sutures and devices for their implantation and extraction have been developed. These devices include needles having various shapes and sizes as well as devices for inserting and removing sutures. The suture material chosen, and the specific type of needle used varies depending on the end use e.g., preparing a graft, closing a laceration etc. When closing a body it is important to minimize tissue trauma and to close quickly. Accordingly, a need exists for a suturing method that will minimize trauma to tissue and save time.

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones (for example, the tibia and the femur) and securing the substitute ligament or graft in the tunnel. To achieve optimal results, it is often important that the substitute ligament or graft be properly tensioned in the graft tunnel. The tension of the graft prior to fixation must be sufficient to achieve stability. Accordingly, a need exists for a method for attaching soft tissue to bone which allows the tendon to be securely placed in a bone tunnel and to remain properly tensioned until the ligaments naturally attach to bone.

BRIEF DESCRIPTION

The invention comprises a method of suturing. Briefly, a portion of a needle having a continuous suture thread running through the eye is advanced through a first location on a first side of a tissue. When the needle is withdrawn from said tissue a suture loop is retained on a second side of said tissue. This can be repeated to obtain as many suture loops as desired on additional locations of the tissue. When all the desired suture loops are formed the needle is advanced all the way through the tissue and a single strand of suture thread is passed through each suture loop on the second side of the said tissue. Thus, one continuous suture forms the suture loop(s) and engages the sutured loops. Depending on the use, if desired, the suture ends are tightened and knotted.

In a preferred embodiment the needle eye, through which the suture thread runs, is located in the tip portion of said needle. It is also preferred that the needle is curved. The tissue may be, for example, a tendon (e.g., patellar), a ligament, or a graft.

When the needle is withdrawn, the suture loop(s) remains on the second side of said tissue. It is contemplated that in certain circumstances and depending on the suture material chosen, it may be desired to mechanically capture the suture loop(s) with forceps or a hook.

In yet another embodiment the suturing method of the present invention involves passing a suture through a tendon to achieve maximum suture fixation strength, as well as a method of securing the tendon to bone that allows for accelerated tendon healing to bone.

The invention also relates to a construct prepared by the suture methods of the present invention. Briefly, a continuous suture thread forms a locking stitch. The suture thread begins in a first location on a first side of a tissue and extends through said tissue to form at least one suture loop on a second side of said tissue. The suture thread extends back to the first side of the tissue and extends back through to the second side of the tissue. The single stranded second end of the continuous suture thread passes through each suture loop on the second side of the said tissue while the single stranded first end remains on the first side of the tissue. The construct can contain as many suture loops as desired. For example, the construct shown in FIG. 7 depicts four suture loops. Thus, one continuous suture forms the suture loop(s) and engages the sutured loops.

BRIEF DESCRIPTION OF THE ACCOMPANYING DRAWINGS

Reference may now be made to the detailed description of preferred embodiments of the invention with follow, taken in conjunction with the accompanying drawings; in which:

FIG. 9 depicts a tissue and a forceps holding a needle having a suture thread through said eye.

FIG. 10 depicts a forceps holding a needle having a suture thread. The needle has been passed partially through a tissue to form a suture loop. A forceps mechanically captures the suture loop.

FIG. 11 depicts a tissue with one suture loop formed. A forceps holding a needle is shown partially passed through the tissue forming a second suture loop. Another forceps is shown capturing said suture loop.

FIG. 12 depicts a method of the present invention used to attach two layers of tissue.

DESCRIPTION OF THE INVENTION

It should be uniformly understood the following detailed descriptions of the present invention and the components, which are illustrated in the figures as generally described below, do not limit the current invention. The current representation is one of several ways the present invention could be designed and carried out. Therefore, the preferred embodiments are intended to only illustrate the present invention and not limit the scope.

Figure 1:
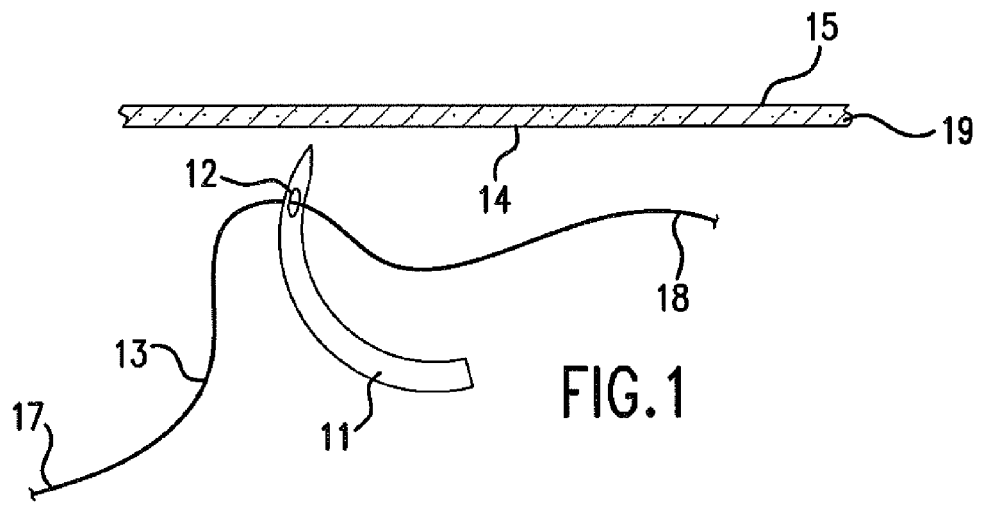
FIG. 1 depicts a partial elevation side view of a tissue and a needle having a suture thread through said eye.
Figure 2:
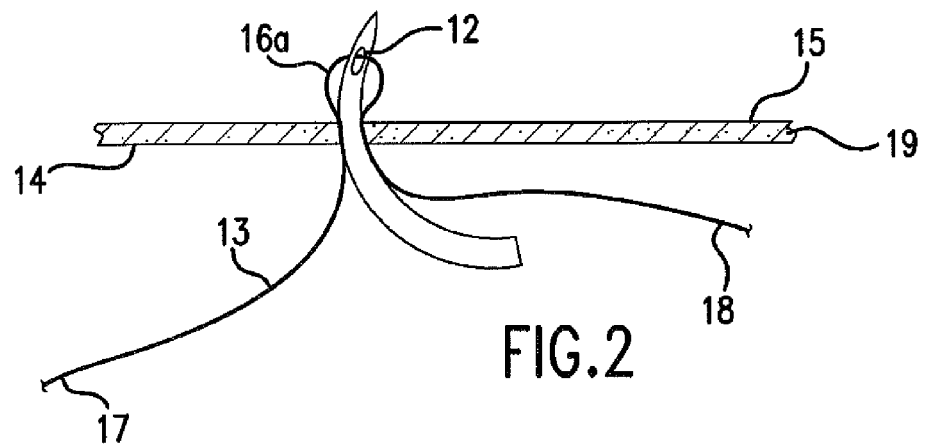
FIG. 2 depicts partial elevation side view of a tissue with a needle having a suture thread. As shown, the needle has been passed partially through a tissue to form a suture loop.
Figure 3:
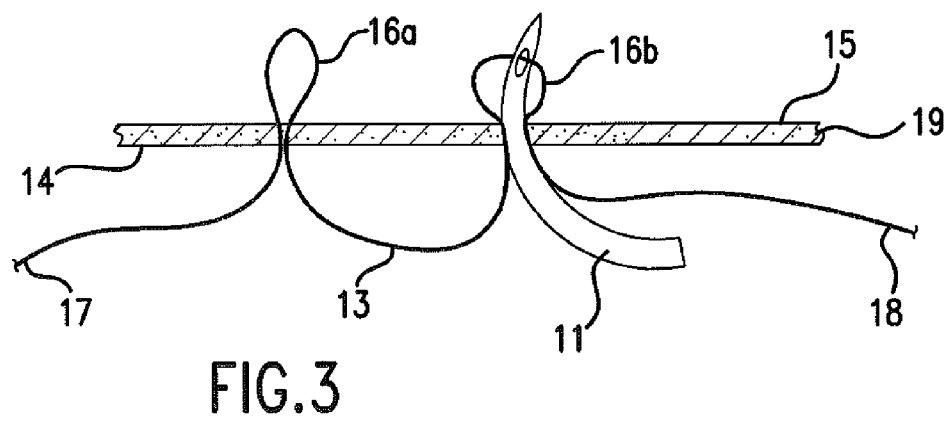
FIG. 3 depicts partial elevation side view of a tissue with one suture loop formed. In an adjacent area of tissue the needle is passed partially through the tissue forming a second suture loop.
Figure 4A:
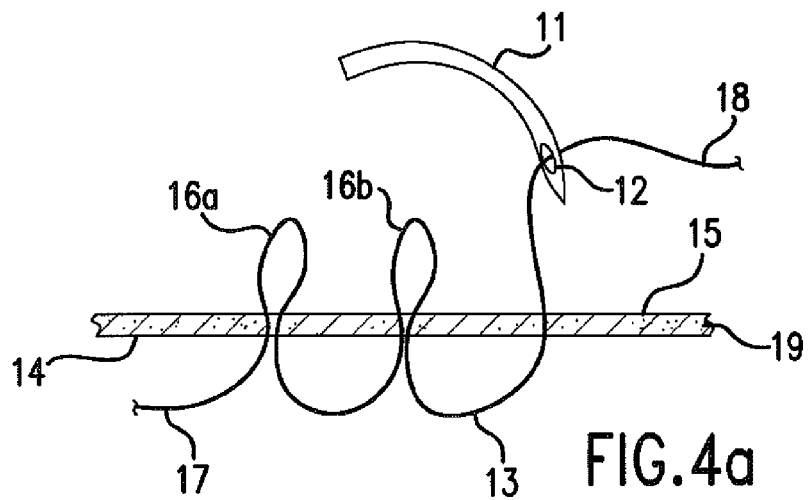
FIG. 4 depicts partial elevation side view of a tissue with two suture loops formed. In an adjacent area of the tissue the needle has been passed completely through the tissue.
Figure 4B:
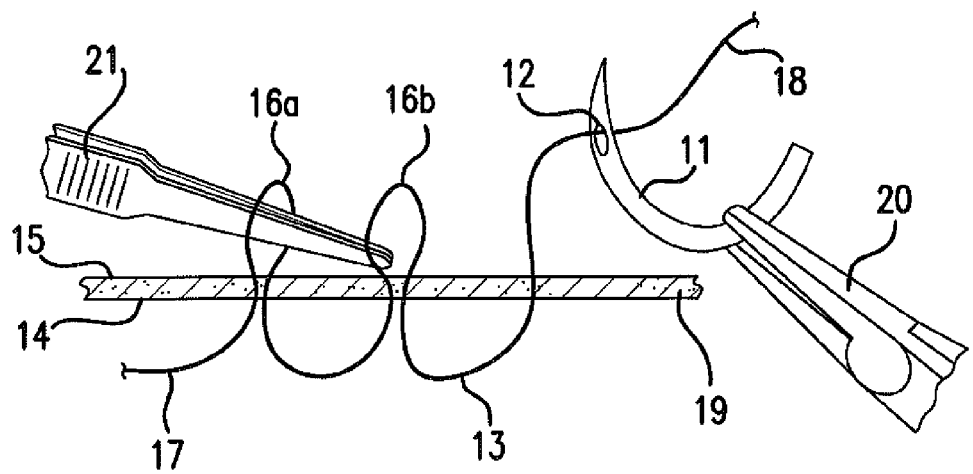
Figure 4C:
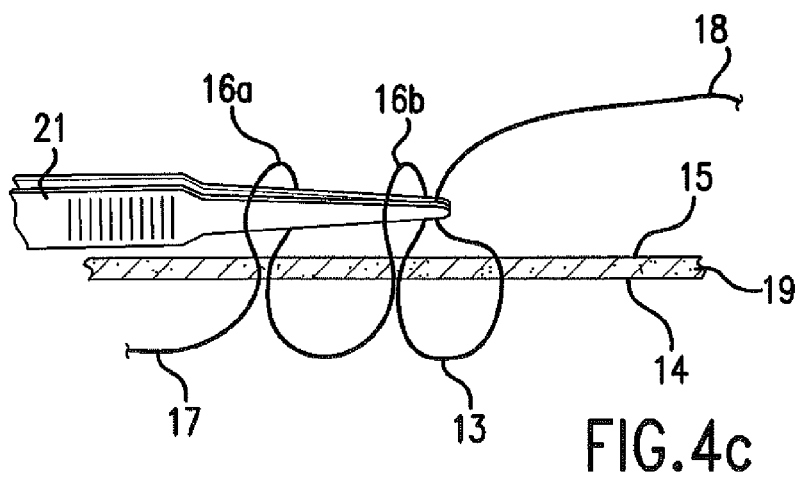
Figure 5:
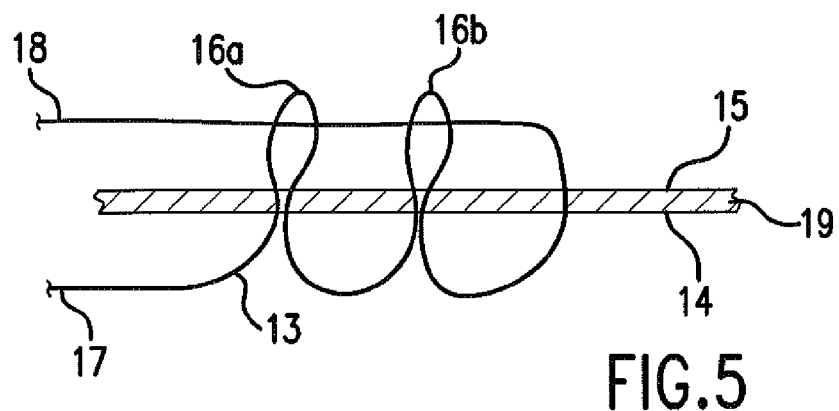
FIG. 5 depicts a partial elevation side view of a tissue with two suture loops remaining on the second side of the tissue with the suture thread passing through and engaging each retained suture loop. One continuous suture thread forms the suture loops and engages the suture loops (6).
Figure 6:
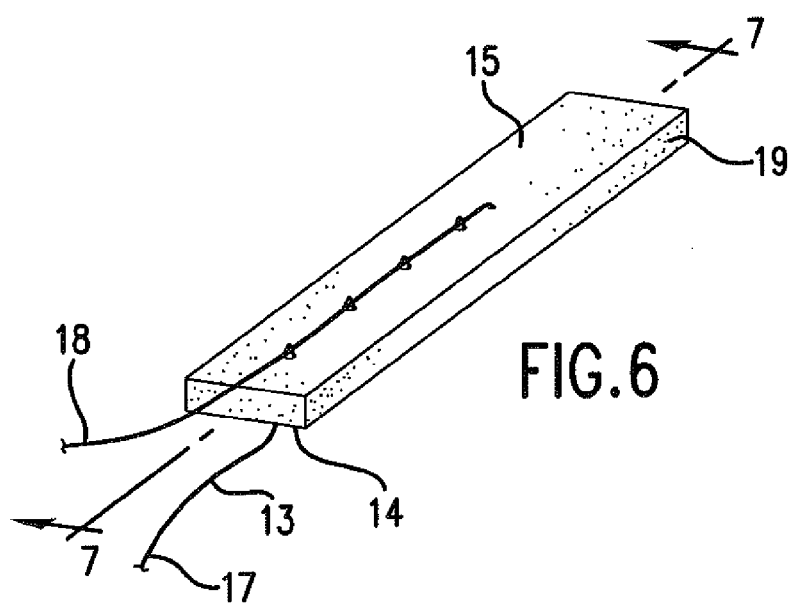
FIG. 6 illustrates a top-side elevation view of a tissue with the suture thread tensioned.
Figure 7:
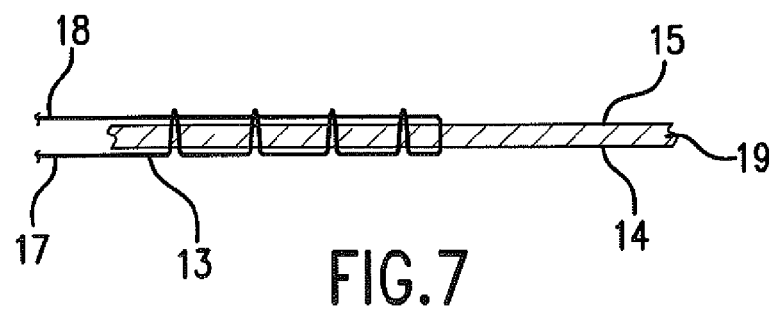
FIG. 7 is a side elevation taken along line 7-7 of FIG. 6.
Figure 8A:
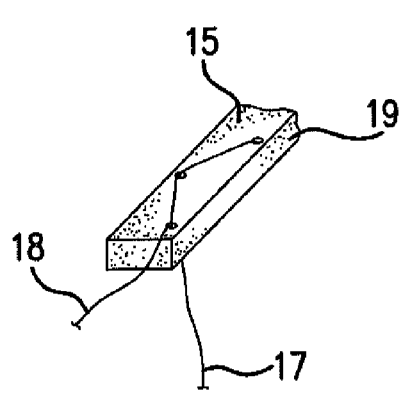
FIG. 8 illustrates a top-side elevation view of a tissue with a two suture thread side-by-side crossed stitch configuration.
Figure 8B:
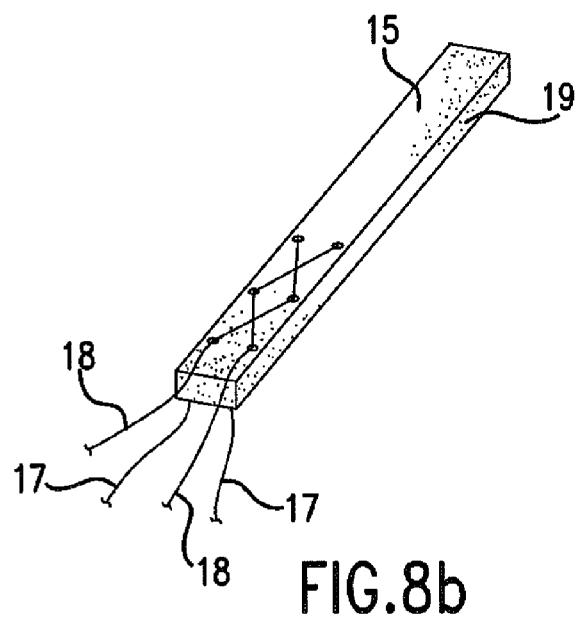
Figure 8C:
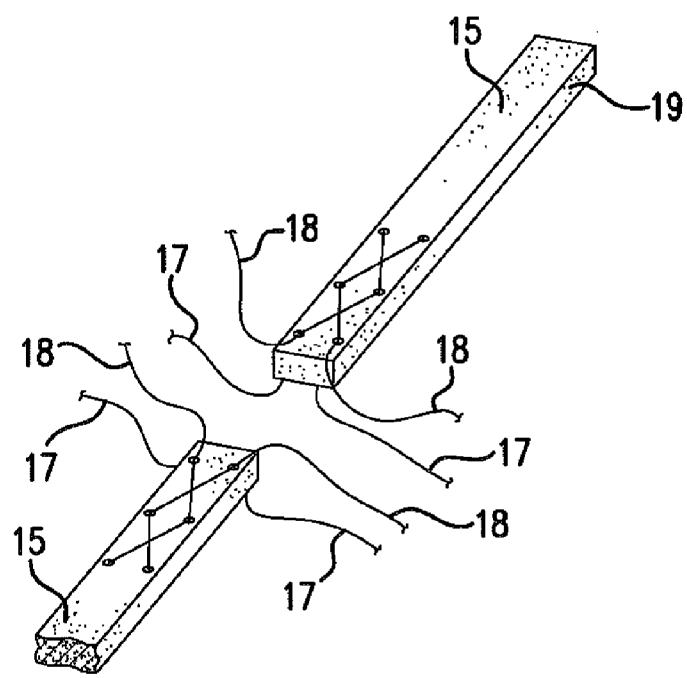

Referring to FIGS. 1-12 in more detail, FIG. 1 depicts a tissue (19) having a first side (14) and second side (15) and a needle (11) having an eye (12) with a suture thread (13) through said eye. FIG. 2 illustrates a needle (11) with a suture thread (13) having been passed partially through a tissue (19). The suture thread (13) forms a suture loop (16a) on the second side (15) of the tissue (19). FIG. 3 illustrates a suture loop (16a) remaining on the second side (15) of the tissue (19) after the needle has been retracted. Adjacent the suture loop (16a) in another portion of tissue, is a needle (11) with suture thread (13) having been passed partially through the tissue (19). The suture thread (13) forms a suture loop (16b) on the second side of the tissue (15). FIG. 4 shows suture loops (16a) and (16b) remaining on the second side (15) of the tissue (19) after the needle has been retracted. Adjacent the suture loop (16a) is second suture loop (16b) in an adjacent portion of the tissue. Adjacent the second suture loop (16b) is a single stand of suture thread which as been passed through said tissue (19). The needle (11) with suture thread (13) has been passed completely through the tissue (19). FIG. 5 illustrates two suture loops (16a) (16b) remaining on the second side of the tissue with the second end (18) of the suture thread passing through and engaging each retained suture loop (16a) (16b) on the second side (15) of the said tissue (19). As can be seen, one continuous suture thread (13) forms the suture loops (16a and 16b) and engages the suture loops (16a and 16b). FIG. 6 illustrates a top-side elevation view of a tissue (19) after the suture loops have been formed and engaged and the continuous suture thread (13) has been tensioned. FIG. 7 is a side elevation taken along line 7-7 of FIG. 6. FIG. 8 illustrates a top-side elevation view of a tissue (19) with a two suture thread side-by-side crossed stitch configuration. This two thread configuration allows the surgeon additional control over the tension and placement of the graft. FIG. 9 depicts a tissue (19) and a forceps (20) holding a needle (11) having a suture thread (13) through said needle eye (12). FIG. 10 depicts a forceps (20) holding a needle (11) having a suture thread (13) thru the eye (12) of said needle (11). The top portion of said needle (11) has been passed partially through a tissue (19) to form a suture loop (16a). A forceps (21) captures the suture loop (6a) mechanically. FIG. 11 depicts a tissue (19) with one suture loop formed (1 &a) and a forceps (20) holding a needle (11) that is shown partially passed through the tissue (19) forming a second suture loop (16b). Another forceps (21) is shown capturing said suture loop (16b). FIG. 12 depicts the method of the present invention used to connect two layers of tissue (19).

As can be seen in the Figures, two thicknesses of suture thread are passed through the tissue when the needle with a suture thread is passed through the tissue. However, only one thickness of suture thread is passed through the suture loop(s) to engage the suture loops and create a locking stitch. Because only one strand of suture thread is used to create the resulting locking stitch the construct resulting from the method of the present invention is extremely stable and the surgeon is able to have considerable control over the tensioning of the resulting locking stitches. Additionally, the stitch construct of the present invention, prepared by a method of the present invention, performed equal to or better than the traditional locking Krakow stitch in load displacement testing (i.e., stiffness (N/mm), failure load (N), displacement at failure (mm) and 3 mm displacement (N)).

As used herein the term "tissue" shall mean any natural or synthetic tissue such as, for example, a muscle, ligament or graft.

The suture loop formation may be continually repeated by means of multiple needle passes until the desired number of suture loops has been formed. One skilled in the art would recognize that the required number of suture loops is case dependent. In some cases only one loop is required and in other cases 2, 3, 4, 5, 6, 7, 8, 9 or 10-20 may be necessary.

The needle (11) may be, for example, straight, half curved or ski, ¼ circle, ⅜ circle, ½ circle, ⅝ circle or compound curve. Most preferably, the needle is ½ circle or ⅜ circle.

Most preferably, the eye of the needle (12) is in the tip or top portion of the needle. The tip portion of the needle is the portion of the needle that partially passes thru the tissue to form a loop. Thus, the eye of the needle is in the portion of the needle that is partially passed through the tissue to form a loop. Most preferably, the eye of the need is closer to the cutting end of said needle than the blunt end of said needle.

Means for manipulating said needle include, for example, forceps to grasp needle end and control the passage of the needle through the tissue, such as shown in FIGS. 9, 10, 11 and 12. Other means for capturing said suture loop on the second side of the tissue include, for example, a hook. Once the needle with suture thread is partially passed through said tissue the suture loop may be captured by mechanical means such as, for example, a forceps or a hook. Any means that will retain the suture loop on the second side of the tissue is contemplated. Certain suture material will allow the suture loop to remain on the second side of the tissue after the needle is withdrawn without any mechanical intervention.

When the method of the present invention is used to close an opening (e.g., cut or laceration) then absorbable suture materials are preferred. Absorbable sutures are those that are broken down such as, for example, chromic "cat gut" or one of the many synthetic absorbable materials made from polymers (e.g., Vicryl and Monocryl). These materials are often broken down non-enzymatically by hydrolysis; water penetrates the suture filaments and causes breakdown of the polymer chain.

Non-absorbable sutures are made of materials that are not readily broken down by the body's enzymes or by hydrolysis. There are naturally occurring non-absorbable materials e.g., silk, cotton, and steel) and synthetic non-absorbable materials (e.g., nylon and Prolene, Mersilene). In some cases they are left in place indefinitely and in other cases they are removed after adequate healing has occurred. The suture thread, which forms the suture loops employed in the method of the present invention, may be formed of any flexible material. In the preferred embodiment, the sutures are formed of a high strength suture material such as FiberWire® suture (Arthrex, Inc.). The high strength suture may be available in various lengths and, preferably, is a #2 FiberWire® suture strand. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. The suture may optionally include filaments of various colors.

In a preferred embodiment, the invention is directed to a novel method of suturing which will provide sutures for an ACL graft preparation. The method can also be used for suturing the free ends of the graft and/or it can be used for suturing the looped end of the graft together.

Additional uses for the method of the present invention include the preparation of a PCL graft (e.g., suturing the free ends of the graft and/or suturing the looped end of the graft together).

The method of the present invention may also be used to prepare other ligament grafts for use in a variety of orthopedic procedures (e.g., ACL).

The method of the present invention may also be used to repair a patellar tendon (e.g., the free end of a torn tendon can be sutured to create a locking stitch and/or the ends can then be tied down to the bone of the patella).

The method of the present invention may also be used to repair an Achilles' tendon (e.g., the free end of the torn tendon can be sutured on each side of the tear to create a locking stitch and/or the ends can then be tied together to affect a repair).

Often, through trauma or attritional degeneration, tendons tear at midsubstance. Thus, the method of the present invention may also be used to repair a midsubstance tendon. Similar to the Achilles' tendon, the ends may be sutured together. In all repairs (Achilles, patella, or midsubstance (such as hand tendon repairs), it is a beneficial aspect of the invention that the suture ends (17, 18) can come out both on top of the tendon and below. This can allow the surgeon to match up the sutures, not just side to side but top to bottom, thus allowing a more secure construct. It is additionally beneficial that the resulting sutures are lower in profile than a locking traditional Krakow stitch. The lower suture profile allows the tendon to slide more easily in the sheath.

In a total hip, for instance, closure is sometimes done with a locking stitch. Thus, the method of the present invention may also be used to close large fascial defects.

As noted above, the suture ends (17, 18) can be used as a graft anchor for securing the graft ligament in place. After the graft ligament is deposed in its proper position, the suture ends may be tied off to secure the graft in its desired place. The suture tying can be used to exert any desired degree of tension on the graft. Graft insertion and fixation may be conducted by employing conventional methods known to one skilled in the art.

The distance between the suture loops, if multiple loops are contemplated, would depend upon the graft or tissue characteristics and the specifics of each surgical intervention. Thus, this invention contemplates any desired distance between the suture loops.

From the foregoing description, one skilled in the art can easily ascertain the essential characteristics of this invention and, without departing from the spirit and scope thereof, can make various changes and modifications of the invention to adapt the method to various other usages and conditions. It should be noted that the above-mentioned description and illustrations of the method of the present invention should by no means be interpreted as the only manner to carry out the present invention. In fact, anyone skilled in the art could foresee a multitude of ways to modify the preferred embodiments. Therefore, the claims set forth are not intended to be restrictive or limit the scope of the invention.

I claim:

1. A method of suturing comprising:
   a) advancing a portion of a needle having a continuous suture through a first location on a first side of a tissue said continuous suture has a first end and a second end,
   b) withdrawing said portion of a said needle from said tissue while capturing a first suture loop on a second side of said tissue wherein said first suture loop remains captured on the second side of said tissue after said needle is withdrawn,
   c) after said needle in b) is withdrawn, advancing said portion of said needle having a continuous suture through a second location on said first side of said tissue,
   d) withdrawing said needle from said second location of said tissue while capturing a second suture loop on said second side of said tissue wherein said second suture loop remains captured on the second side of said tissue after said needle is withdrawn,
   e) optionally repeating steps a and b thru additional locations on the tissue,
   and
   f) after all desired suture loops created in any of steps b-e have been captured advancing said needle all the way through said tissue and passing the second end of the continuous suture through all captured suture loops on the second side of said tissue wherein one said continuous suture forms the captured suture loops and engages the captured suture loops.

2. A method according to claim 1, wherein the needle eye is located in the tip portion of said needle.

3. A method according to claim 1, wherein after said continuous suture engages the suture loop(s) the first and second suture ends are tightened and knotted.

4. A method according to claim 1, wherein the tissue is a tendon or a ligament.

5. A method according to claim 4, wherein said ligament is a graft.

6. A method according to claim 4, wherein said tendon is patellar tendon.

7. A method according to claim 1, wherein said loop is captured with a forceps or a hook.

8. A method according to claim 1, wherein said needle is curved.

9. A graft preparation for an ACL repair prepared by the method according to claim 1.

10. A graft preparation for an PCL repair prepared by the method according to claim 1.

* * * * *